United States Patent [19]

Atwell et al.

[11] Patent Number: 4,474,961
[45] Date of Patent: Oct. 2, 1984

[54] 1,10[8,9-BENZ]PHENANTHROLINE

[75] Inventors: Graham J. Atwell; Bruce C. Baguley; William A. Denny, all of Auckland, New Zealand

[73] Assignee: Development Finance Corporation of New Zealand, Wellington, New Zealand

[21] Appl. No.: 469,273

[22] Filed: Feb. 24, 1983

[30] Foreign Application Priority Data

Mar. 2, 1982 [NZ] New Zealand .................. 199887

[51] Int. Cl.³ .................................. C07D 471/04
[52] U.S. Cl. ................................ 546/70; 427/258
[58] Field of Search ............................... 546/70

[56] References Cited

OTHER PUBLICATIONS

Cain et al., "J. Med. Chem", 18, 1110–7, (1965).
Dawson et al., J. Chem. Soc., pp. 150–155, 1946.
Elslager et al., "J. Med. Pharm. Chem.", vol. 5, pp. 546–558, 1962.

Primary Examiner—Richard Raymond
Assistant Examiner—D. B. Springer
Attorney, Agent, or Firm—Brumbaugh, Graves, Donohue & Raymond

[57] ABSTRACT

Compounds represented by the general formula (I)

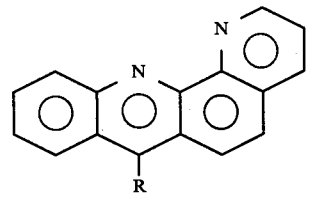

in which R represents an aniline substituted in the para position by either —NHSO₂CH₃ or —NHCOOCH₃ and bearing either an —H or —OCH₃ in the ortho position, or an aniline substituted in the para position by —NH-P(O)(OCH₃)₂ and bearing an —H in the ortho position, and the acid addition salts thereof, have antitumor activity.

6 Claims, No Drawings

1,10[8,9-BENZ]PHENANTHROLINE

BACKGROUND TO THE INVENTION

A number of derivatives of acridine have recently been studied for antitumour activity. In earlier work with the 9-anilinoacridines the marked antitumour effect of the 1′-methanesulphonamide derivative 4′-(9-acridinylamino) methanesulphonanilide or AMSA was revealed (G. J. Atwell, B. F. Cain and R. N. Seelye, J.Med. Chem., 15, 611–615 (1972). A search for more dose-potent congeners culminated in the development of the clinical agent 4′-(9-acridinylamino) methanesulphon-m-aniside, m-AMSA or amsacrine. (See the following articles: B. F. Cain and G. J. Atwell, Europ. J. Cancer 10, 539–549 (1974); B. F. Cain, G. J. Atwell and W. A. Denny, J.Med.Chem., 18, 1110–1117 (1975); B. F. Cain, W. R. Wilson and B. C. Baguley, Molecular Pharmacology, 12, 1027–1035 (1976); B. F. Cain, G. J. Atwell and W. A. Denny, J.Med.Chem., 19, 772–777 (1976); B. F. Cain and G. J. Atwell, J.Med.Chem., 19, 1409–1416 (1976); M. J. Waring, Europ.J. Cancer, 12, 995–1001 (1976); B. C. Baguley, W. R. Wilson, L. R. Ferguson and B. F. Cain, Current Chemotherapy, pp.1210–1212 (1978); W. A. Denny, G. J. Atwell and B. F. Cain, J.Med.Chem., 21, 5–10 (1978).)

The antitumour activity of a large range of AMSA and m-AMSA analogues containing variously substituted acridine nuclei has now been investigated, see for example G. J. Atwell, B. F. Cain and R. N. Seelye, J.Med.Chem., 15 611–615 (1972); B. F. Cain, R. N. Seelye and G. J. Atwell, J.Med.Chem., 17, 922–930 (1974); B. F. Cain, G. J. Atwell and W. A. Denny, J.Med.Chem., 18, 1110–1117 (1975), and J.Med.Chem., 19, 772–777 (1976); B. F. Cain and G. J. Atwell, J.Med.-Chem., 19, 1124–1129 and 1409–1416 (1976); G. J. Atwell, B. F. Cain and W. A. Denny, J.Med.Chem., 20, 520–526, 987–996, 1128–1134, and 1242–1246 (1977); W. A. Denny, G. J. Atwell and B. F. Cain, J.Med.Chem., 21, 5–10 (1978); W. A. Denny and B. F. Cain, J.Med.-Chem., 21, 430–437 (1978); B. F. Cain, B. C. Baguley and W. A. Denny, J.Med.Chem., 21, 658–668 (1978); L. R. Ferguson and W. A. Denny, J.Med.Chem., 22, 251–255 (1979); W. A. Denny, G. J. Atwell and B. F. Cain, J.Med.Chem., 22, 1453–1460 (1979); L. R. Ferguson and W. A. Denny, J.Med.Chem., 23, 269–274 (1980); B. C. Baguley, W. A. Denny, G. J. Atwell and B. F. Cain, J.Med.Chem., 24, 520–525 (1981); L. R. Ferguson and B. C. Baguley, Mutation Research, 82, 31–39 (1981); W. A. Denny, B. F. Cain, G. J. Atwell, C. Hansch, A. Panthananickal and A. Leo, J.Med.Chem., 25, 276–315 (1982); B. F. Cain, G. J. Atwell, B. C. Baguley and W. A. Denny, U.S. Pat. application Ser. No. 386,104, filed June 7, 1982 as a continuation-in-part of U.S. Pat. application Ser. No. 187,517 filed Sept. 15, 1980; and B. F. Cain and G. J. Atwell, U.S. Pat. No. 4,366,318, issued Dec. 28, 1982. During this work a number of derivatives containing different oxygen-containing substituents were evaluated at the 1′-position (e.g. NHCOCH3, NHCOOCH3, COOH) but these compounds were less active and/or less dose potent than those bearing the methanesulphonamide (B. C. Baguley, W. A. Denny, G. J. Atwell and B. F. Cain, J.Med.Chem., 24, 170–177 (1981).

The preparation of various 7-amino and 7-(mono-and dialkylaminoalkylamino)-benzo [b][1,10] phenanthrolines and the evaluation of these compounds for antimalarial and antiamebic properties has been reported J. Dobson and W. O. Kermack, J.Chem.Soc. pp 150–155 (1946) and E. F. Elslager and F. H. Tendick, J.Med.-Pharm.Chem., 5, pp 546–558 (1962).

SUMMARY OF THE INVENTION

We have now found a novel group of derivatives of 1,10-phenanthroline which have antitumour activity.

It is the object of the present invention to provide novel 1,10-phenanthroline derivatives, bearing substituted anilines off the 7-position and having antitumour activity, processes for the preparation of these compounds, and the use of these compounds as antitumour agents.

DESCRIPTION OF THE INVENTION

The novel 1,10-[8,9-benz] phenanthroline derivatives of the present invention are the compounds represented by the general formula (I):

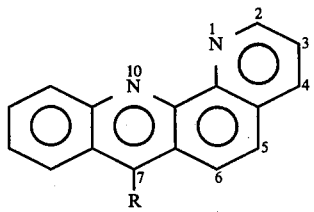

in which R represents an aniline substituted in the para position with either —NHSO$_2$CH$_3$ or —NHCOOCH$_3$ and bearing either an —H or —OCH$_3$ at the ortho position, or an aniline substituted in the para position with —NHP(O)(OCH$_3$)$_2$ and bearing an —H at the ortho position, and acid addition salts thereof.

The compounds of the invention form pharmaceutically acceptable salts with both organic and inorganic acids. Examples of suitable acids for salt formation are hydrochloric, hydrobromic, sulfuric, phosphoric, acetic, citric, oxalic, malonic, salicylic, malic, fumaric, succinic, ascorbic, maleic, methanesulfonic, gluconic, 2-hydroxyethanesulphonic and the like acids.

The compounds of formula (I) may be prepared by the acid-catalysed coupling of a 7-substituted 1,10-[8,9-benz]-phenanthroline with the appropriate aniline compound.

Accordingly, the compounds of formula (I), and the acid addition salts thereof, are prepared by a process which comprises the acid-catalysed coupling of a 7-substituted 1,10-[8,9-benz]phenanthroline of formula (II),

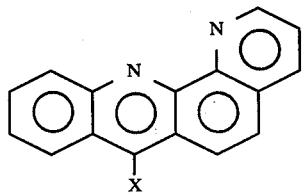

where X is any suitable leaving group (e.g. methoxy, phenoxy, tosyl or halogen) but preferably chloro, with a substituted aniline of general formula (III),

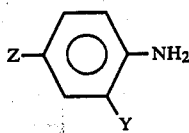

where Y is —H or —OCH₃ and Z is either —NHSO₂CH₃ or —NHCOOCH₃ or where Y is —H and Z is —NHP(O)(OCH₃)₂, and, if desired, converting an acid addition salt of a compound of formula (I) into the free base compound of formula (I) and/or converting a compound of formula (I) into an acid addition salt thereof.

The acid-catalysed coupling reaction of compound (II) with compound (III) is performed preferably in an anhydrous solvent, for example methanol, ethanol, 2-ethoxyethanol or N-methylpyrrolidone, with methanol being preferred, at temperatures preferably between 30° C. and 60° C. The reaction is preferably catalysed by adding one or two drops of concentrated hydrochloric acid to the mixture of compound (II) and compound (III) to initiate the reaction.

The acid addition salts are prepared by contacting the free base form with an equivalent amount of the desired acid in the conventional manner. The free base forms may be regenerated by treating the salt form with a base. For example, dilute aqueous base solutions may be utilized. Dilute aqueous potassium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for the purposes of the present invention.

The 7-chlorophenanthroline of formula (II, X=Cl) may be prepared by treatment of N-(8-quinolyl) anthranilic acid with SOCl₂ or POCl₃. The 7-bromophenanthroline of formula (II, X=Br) can be prepared from either N-(8-quinolyl) anthranilic acid by treatment with phosphoryl bromide or from the pyridoacridone by reaction with thionyl bromide. 7-Phenoxy- and 7-methoxy-phenanthrolines can be prepared by the methods given in Albert "The Acridines", 2nd Edition, Edward Arnold Ltd., London (1966).

The substituted aniline of formula (III) and the substituted aniline group represented by R in formula (I) is selected from 2-methoxy-4-methanesulphonamidoaniline, 4-methanesulphonamidoaniline, 2-methoxy-4-methylcarbamoylaniline, 4-methylcarbamoylaniline and 4-dimethoxyphosphoramidoaniline.

4-Methanesulphonamidoaniline (III, Y=H, Z=NHSO₂CH₃), 2-methoxy-4-methanesulphonamidoaniline (III, Y=OCH₃, Z=NHSO₂CH₃) and 4-methylcarbamoylaniline (III, Y=H, Z=NHCOOCH₃) are known compounds. 4-Dimethoxyphosphoramidoaniline (III, Y=H, Z=NHP(O)(OCH₃)₂) may be prepared from p-nitroaniline as described in G. W. Rewcastle, G. J. Atwell, B. C. Baguley and W. A. Denny, U.S. patent application Ser. No. 409,594, filed Aug. 19, 1982.

The compound of formula (III) wherein Y represents OCH₃ and Z represents NHCOOCH₃, i.e. 2-methoxy-4-methylcarbamoylaniline, is a novel compound and forms part of the present invention.

2-Methoxy-4-methylcarbamoylaniline is prepared by the general method outlined in Scheme I in which R¹ represents an alkyl group, and this general process also forms part of the present invention.

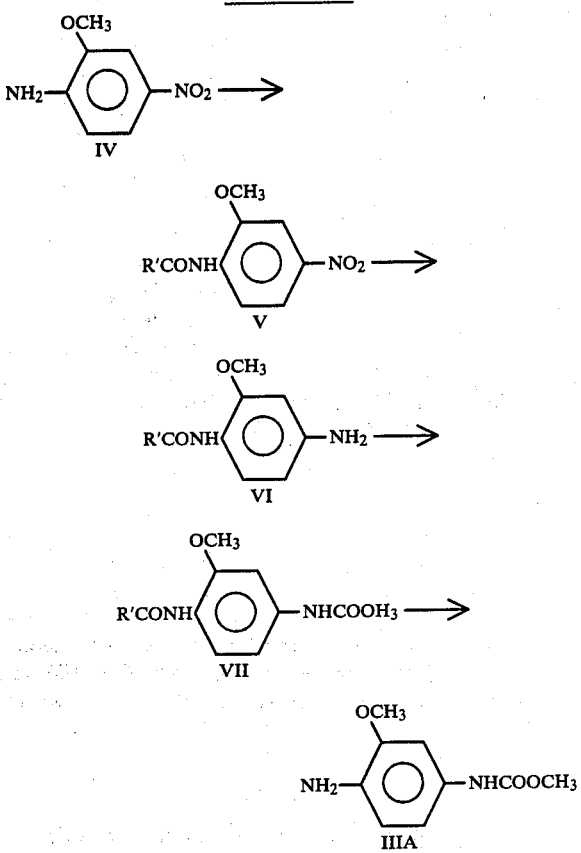

Commercially available 2-methoxy-4-nitroaniline (IV) is acylated to an N-alkylanilide (preferably to the N-n-butyranilide) to provide (V) of suitable lipophilic character to facilitate easy handling. Reduction with Fe/HCl in aqueous ethanol gives (VI), which is treated with methyl chloroformate in pyridine or ethanol to give (VII). Acid hydrolysis yields the aniline (IIIA). The following Table I sets out physicochemical data for the five phenanthroline derivatives of formula (I). In Table I the following terms and abbreviations are used:
MW=molecular weight
MP=melting point of the reported acid addition salt in °C.

TABLE I

| No. | R | MP | Formula | MW |
|-----|---|----|---------|----|
| 1 | 2-methoxy-4-methane-sulphonamidoaniline | 210–212 | C₂₄H₂₀N₄O₃S.HCl 1.5H₂O | 507.4 |
| 2 | 4-methanesulphonamidoaniline | 305–307 | C₂₃H₁₈N₄O₂S.HCl | 450.7 |
| 3 | 2-methoxy-4-methyl carbamoyl-aniline | 272–275 | C₂₅H₂₀N₄O₃.HCl | 460.7 |
| 4 | 4-methylcarbamoyl aniline | 280–285 | C₂₄H₁₈N₄O₂.HCl | 430.6 |
| 5 | 4-dimethoxyphosphor-amido-aniline | 262–265 | C₂₄H₂₁N₄O₃P.HCl | 480.7 |

The following Example A illustrates the preparation of compound 1 of Table I, (where R is 2-methoxy-4-methanesulphonamidoaniline) and acid addition salts thereof. Example B illustrates the preparation of compound 3 of Table I, (where R is 2-methoxy-4-methylcarbamoylaniline).

EXAMPLE A. PREPARATION OF COMPOUND 1 OF TABLE I

N-(8-quinolyl) anthranilic acid

8-Nitroquinoline (5.1 g, 29.3 mM), was reduced at 20° C. over Pd/C catalyst until uptake of $H_2$ ceased (10 min). The solution was filtered and evaporated to dryness, and to the residue was added o-chlorobenzoic acid (4.5 g, 28.8 mM), $K_2CO_3$ (29.3 mM), and CuO (0.1 g). The mixture was suspended in 2-ethoxyethanol (5 mL), and stirred for 2 hr at 140° C. The cooled mixture was dissolved in water (10 mL) and acidified with conc. HCl. After removal of tarry material, the filtrate was treated with charcoal, filtered and the pH adjusted to 6 with aqueous ammonia. The resultant product was collected, washed well with water and recrystallized from ethanol as yellow needles (3.5 g, 46%) mp 247°–248° C. Anal (C,H,N) for $C_{16}H_{12}N_2O_2$.

1,10-[8,9-benz]-7-chlorophenanthroline (II, X=Cl)

The above acid (1.5 g, 5.7 mM) was refluxed with excess $POCl_3$ (5 mL) for one hour. The volatiles were evaporated under vacuum, and the residue was dissolved in $CHCl_3$ and poured into excess ice cold dilute ammonia. The organic layer was separated, dried, and concentrated to small volume (15 mL). This was diluted with hot petroleum ether (X-2 fraction, 150 mL), the resulting mixture was boiled briefly, filtered, and the solvent evaporated at low temperature to give the chloroheterocycle as a yellow solid (0.95 g, 60%).

COMPOUND 1 OF TABLE I

A mixture of 1,10-[8,9-benz]-7-chlorophenanthroline (II,X=Cl) (0.95 g, 3.4 mM) and 2-methoxy-4-methanesulphonamidoaniline (III, Y=OCH_3, Z=NHSO_2CH_3) (0.8 g, 3.7 mM) in dry N-methylpyrrolidone (5 ml) was treated with a drop of conc. HCl and warmed to 50° C. for 20 minutes. The cooled blood-red solution was diluted with ethyl acetate, and the resulting oil collected by decantation of the supernatant and washed with ethyl acetate. It was then dissolved in dry methanol (30 mL) and a drop of conc. HCl, filtered, and heated to boiling. Hot ethyl acetate was added slowly to the boiling solution until crystallization commenced. After standing for 6 hours at 20° C., the deep red hydrochloride addition salt was collected (1.3 g, 80%) (mp 212°–215° C.).

The above hydrochloride salt could also be crystallized from hot water where the pH had been adjusted to 3 by addition of hydrochloric acid; the yellow product obtained by this method had mp 210°–212° C., and analysed (C,H,N,Cl) for formula $C_{24}H_{20}N_4O_3S\cdot HCl\cdot 1.5 H_2O$.

For conversion of the above initially-obtained hydrochloride salt to other pharmaceutically acceptable acid addition salts, the compound is dissolved in a suitable amount of aqueous ethanol by warming, cooled to 20° C. and an aqueous solution of sodium hydrogen carbonate (1.1 equivalents) added with stirring. After stirring for one hour, the free base is collected, washed well with water and dried. The free base is then stirred with methanol and 1.1 equivalents of the desired acid until a solution is formed. Following filtration, the acid addition salt is precipitated by addition of ethyl acetate.

EXAMPLE B. PREPARATION OF COMPOUND 3 OF TABLE I

2-methoxy-4-methylcarbamoylaniline

N'-(n-Butyramido)-2-methoxybenzene-1,4-diamine (VI) (20.8 g, 100 mM) in refluxing acetone (200 ml) containing MgO (5 g) was treated dropwise with methyl chloroformate (10 g, 106 mM). After all the reagent was added the mixture was heated under reflux for a further 30 min, cooled and filtered. The filtrate was evaporated and the residue crystallized from aqueous EtOH to give pure carbamate (VII) (21 g, 80% yield), mp. 141°–142° C.

The above carbamate (4 g, 15 mM) was heated under reflux in 2N aqueous HCl for 3 hours. The residue after evaporation was crystallized once from water and once from benzene/petroleum ether to give 2-methoxy-4-methylcarbamoylaniline (III, Y=OCH_3, Z=NHCOOCH_3) (2.7 g, 93% yield), m.p. 122°–124° C.

COMPOUND 3 OF TABLE I

A mixture of this 2-methoxy-4-methylcarbamoylaniline (1.2 g, 5.6 mM) and 1,10-[8,9-benz]-7-chlorophenanthroline (II, X=Cl) (15 g, 54. mM) was suspended in dry MeOH (100 ml) and boiled gently until all dissolved. A trace of HCl was added, and the mixture was boiled for 5 minutes. EtOAc was added dropwise to the boiling solution until turbidity, and the reaction was allowed to cool, giving the hydrochloride salt of compound 3 as red needles (2.2 g, 90% yield), mp 272°–275° C.

The compounds of formula (I) show good antitumour activity in animal systems, as seen in Table II, using the lymphocytic leukemia P388 and lymphocytic leukemia L1210 test systems. These have been shown by studies at the National Cancer Institute, U.S.A. to be useful for detecting agents with antitumor activity against clinical cancer (A. Goldin, J. M. Venditti, J. S. MacDonald, F. M. Mugia, J. E. Henney and V. T. De Vita, *Europ.J.Cancer* 17, 129–142, (1981). The abbreviations given in Table II are:

P388 in vivo—Tumour P388 cells were obtained as frozen stocks from Mason Research Inc., U.S.A. and passaged intraperitoneally according to standard methods (Cancer Chemother. Rep. 3, Part 3, page 9, 1972) in DBA-2 mice of either sex. Groups of six F1 hybrid mice (DBA-2 male×C57 B1 female, g weight 20±1 g) were injected intraperitoneally with $10^6$ cells on day 0.

O.D.—optimal drug dose, in milligrams per kilogram, administered as a solution in 0.1 ml of 30% v/v ethyl alcohol in water on days 1, 5 and 9 after tumour inoculation. The drug is administered as a soluble acid addition salt.

ILS—percentage increase in life span of treated animals over that of groups of control animals injected with tumour alone. The average survival of control mice was 11 days. Values of ILS greater than 20% are considered statistically significant.

L1210 in vitro—The culture methods used are described in detail elsewhere (B. C. Baguley and R. Nash, *Europ.J.Cancer*, 17, 671–679 (1981). Acceptable reproducibility of data depends critically upon the maintenance of optimal culture conditions. L1210 cells were initially obtained from Dr. I. Wodinsky, Arthur D. Little Inc., Boston, U.S.A., under the auspices of the National Cancer Institute.

ID$_{50}$—the nanomolar concentration of drug which when added to cultures of murine L1210 leukaemia cells over a period of 70 hours, reduces the resultant counted number of leukaemia cells by 50% (B. C. Baguley and R. Nash, *Europ.J.Cancer* 17, 671–679 (1981).

TABLE II

| | Biological data for the compounds of Table I | | | |
|---|---|---|---|---|
| | L1210 in vitro | P388 in vivo | | |
| No. | ID$_{50}$ | OD | ILS | Active |
| 1 | 26 | 13.3 | 109 | Yes |
| 2 | 58 | 150 | 30 | Yes |
| 3 | 46 | 45 | 95 | Yes |
| 4 | 18 | 30 | 64 | Yes |
| 5 | 31 | 45 | 64 | Yes |

It is clear from the data of Table II that the 1,10-phenanthroline derivatives of general formula (I) are active antitumour agents, giving significant levels of life extension when tested against the P388 leukaemia system when given by intraperitoneal injection. The compounds also show antitumour activity when given by oral and intravenous routes. They also show high cytotoxicity towards cultured L1210 leukaemia cells (Table II), and are active in a number of cultured tumour cell lines, including those originating from human colon and breast tumours.

These compounds are thus indicated for use as antitumour agents, and the present invention also provides pharmaceutical compositions having antitumour activity and comprising at least one compound of the general formula (I) or a pharmaceutically acceptable acid addition salt thereof, and one or more pharmaceutically acceptable carriers or diluents.

The present invention further provides a method for treating tumours in a patient which comprises administering to the patient an antitumour effective amount of a compound of the general formula (I) or a pharmaceutically acceptable acid addition salt thereof.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2 and about 60% of the weight of the unit. The amount of active compound in such therapeutically useful compositions is such that a suitable dosage will be obtained. Preferred compositions or preparations according to the present invention are prepared so that an oral dosage unit form contains between about 5 and about 200 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmaceutically acceptable salt can be prepared in water suitably mixed with a surfactant such as hydroxpropylcellulose. Dispersions can also be prepared in glycerol, liquid polyethylene glycols, and mixtures thereof and in oils. Under ordinary conditions of storage and use, these preparations contain a presevative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the free-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. "Dosage unit form" as used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg, with from about one to about 30 mg being preferred. Expressed in proportions, the active compound is generally present in from about 0.1 to about 400 mg/ml of carrier. In the case of compositions containing supplementary active ingredients, the dosages are determined by reference to the usual dose and manner of administration of the said ingredients.

What is claimed is:
1. A compound represented by the general formula (I)

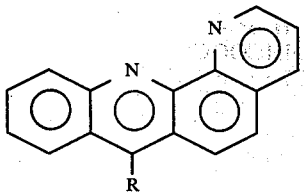

in which R represents an anilino substituted in the para position by either —NHSO$_2$CH$_3$ or —NHCOOCH$_3$ and bearing either an —H or —OCH$_3$ in the ortho position, or an anilino substituted in the para position by —NHP(O)(OCH$_3$)$_2$ and bearing an —H in the ortho position, or a pharmaceutically acceptable acid addition salt thereof.

2. A compound according to claim 1 in which R is 2-methoxy-4-methanesulphonamidoanilino.

3. A compound according to claim 1 in which R is 4-methanesulphonamidoanilino.

4. A compound according to claim 1 in which R is 2-methoxy-4-methylcarbamoylanilino.

5. A compound according to claim 1 in which R is 4-methylcarbamoylanilino.

6. A compound according to claim 1 in which R is 4-dimethoxyphosphoramidoanilino.

* * * * *